United States Patent
Wankhade et al.

(10) Patent No.: US 11,497,690 B2
(45) Date of Patent: Nov. 15, 2022

(54) WATER-IN-OIL MICROEMULSIONS FOR PERSONAL CARE

(71) Applicant: GALAXY SURFACTANTS LTD., Mumbai (IN)

(72) Inventors: Arpit Wankhade, Amravati (IN); Bhagyesh Jagannath Sawant, Kalyan (IN); Nirmal Koshti, Piscataway, NJ (US)

(73) Assignee: GALAXY SURFACTANTS LTD., Navi Mumbai (IN)

( * ) Notice: Subject to any disclaimer, the term of this patent is extended or adjusted under 35 U.S.C. 154(b) by 0 days.

(21) Appl. No.: 16/077,008

(22) PCT Filed: May 2, 2016

(86) PCT No.: PCT/IN2016/000113
§ 371 (c)(1),
(2) Date: Aug. 9, 2018

(87) PCT Pub. No.: WO2017/081698
PCT Pub. Date: May 18, 2017

(65) Prior Publication Data
US 2019/0083370 A1    Mar. 21, 2019

(30) Foreign Application Priority Data
Nov. 14, 2015    (IN) .................. 4318/MUM/2015

(51) Int. Cl.
| | |
|---|---|
| *A61K 8/06* | (2006.01) |
| *A61K 8/39* | (2006.01) |
| *A61K 8/46* | (2006.01) |
| *A61Q 5/02* | (2006.01) |
| *A61Q 5/12* | (2006.01) |
| *A61Q 19/10* | (2006.01) |
| *A61K 8/92* | (2006.01) |
| *A61K 8/44* | (2006.01) |

(52) U.S. Cl.
CPC ................ *A61K 8/068* (2013.01); *A61K 8/39* (2013.01); *A61K 8/44* (2013.01); *A61K 8/463* (2013.01); *A61K 8/922* (2013.01); *A61K 8/925* (2013.01); *A61Q 5/02* (2013.01); *A61Q 5/12* (2013.01); *A61Q 19/10* (2013.01); *A61K 2800/262* (2013.01); *A61K 2800/596* (2013.01); *A61K 2800/72* (2013.01)

(58) Field of Classification Search
CPC . A61K 8/068; A61K 8/39; A61K 8/44; A61K 8/463; A61K 8/925; A61K 2800/262; A61K 2800/596; A61K 2800/72; A61Q 5/02; A61Q 5/12; A61Q 19/10
See application file for complete search history.

(56) References Cited

U.S. PATENT DOCUMENTS

| | | |
|---|---|---|
| 4,835,002 A | 5/1989 | Wolf et al. |
| 2004/0101498 A1 | 5/2004 | Koshti et al. |
| 2004/0234484 A1* | 11/2004 | Peffly et al. ............. A61K 8/20 424/70.13 |
| 2006/0122322 A1* | 6/2006 | Chrisstoffels ........ A61K 8/8158 524/804 |
| 2010/0267598 A1* | 10/2010 | Sans et al. ............. A61K 8/345 510/130 |

FOREIGN PATENT DOCUMENTS

DE    102006004955 A1    7/2007

OTHER PUBLICATIONS

Fregonesi, Adriana, et al. "Brazilian oils and butters: The effect of different fatty acid chain composition on human hair physiochemical properties." J Cosmet Sci 60.2 (2009): 273-80.*

* cited by examiner

*Primary Examiner* — Frederick F Krass
*Assistant Examiner* — Amanda Michelle Petrirsch
(74) *Attorney, Agent, or Firm* — Kramer & Amado, P.C.

(57) ABSTRACT

Water-in-oil microemulsions containing triglyceride oil for personal care applications are described. The W/O type of microemulsions based on triglyceride oils such as soya oil and sunflower oil are suitable for skin cleansing shower oils. The microemulsions of the patent application allow the use of several mild surfactants, thereby obviating the use of aliphatic amine based anionic surfactants for personal cleansing. The microemulsion based on coconut oil serves like a 'two-in-one' formulation for prewash hair conditioning like a typical hair-oil and subsequently like a shampoo for cleansing the hair.

13 Claims, 1 Drawing Sheet

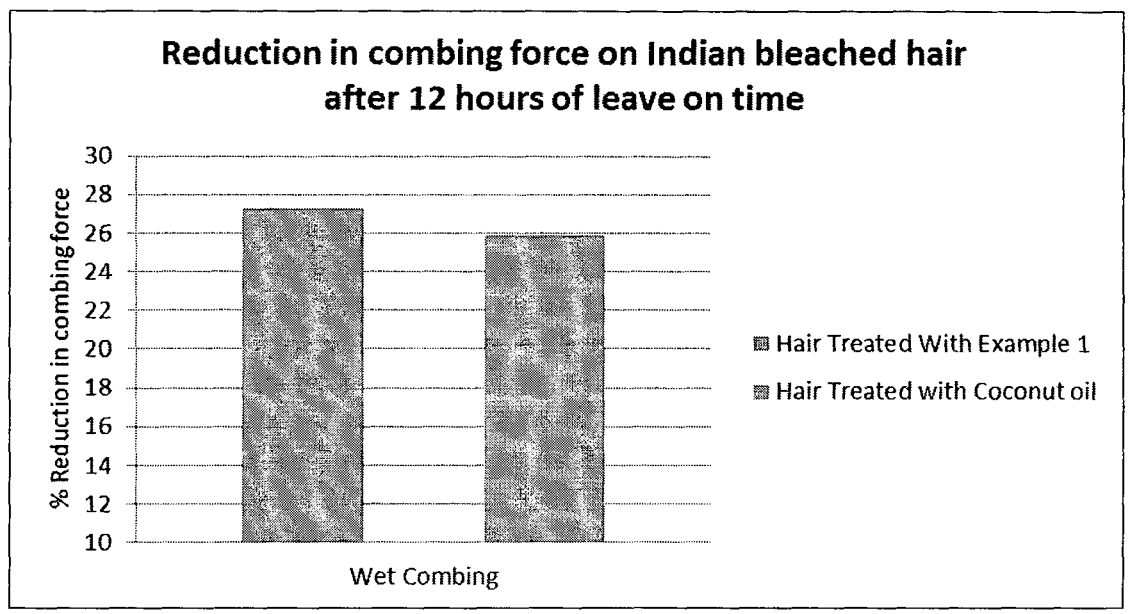

WATER-IN-OIL MICROEMULSIONS FOR PERSONAL CARE

FIELD OF INVENTION

The present invention relates to microemulsions for personal care products using triglyceride type of oils. In particular, the present invention relates to microemulsion compositions with triglyceride oils such as soya bean, sunflower, olive etc. for skin cleansers.

It also relates to microemulsions based on coconut oil that are used in conditioning-cum-cleansing 'hair oil' formulations.

The microemulsions of the present invention employ surfactants that are free of toxic aliphatic amines.

BACKGROUND OF INVENTION

Skin Care Products

Oil based skin cleansers are the mildest cleansers since they do not strip away stratum corneum's lipids and water-soluble NMF (natural moisturizing factor) of stratum corneum that maintains skin's hydration.

There are several shower oils available in market. The examples are Beiersdorf's Nivea range has Pampering Shower Oil and Natural Shower Oil and Eucerin Calming Foaming Shower oil, No. 7 Luxurious Foaming oil from Boots and L'Occitane's Almond Supple Skin Oil. Shower oils comprising oil-compatible surfactants are known for a long time (BE 08700824, EP 0876176 and DE 10156674). US Patent application 2005/0192190A1 gives several examples of shower oil with monoisopropanol amine (MIPA) laureth sulphate (Formula I; R=$C_7$), with Laureth-4 and, cocoamide diethanolamine (CDEA) (Zetesol 100, Zschimmer and Schwarz). U.S. Pat. No. 8,383,090 teaches skin cleansers based on oils where anionic surfactants are made oil-compatible by neutralizing acyl sarcosines with various amines such as monoisopropanol amine (MIPA), triisopropanol amine (TIPA), aminomethyl propanediol (AMPD) and aminomethyl propanol (AMP). Another oil shower bath composition suggested by Wulfinghoff (Euro cosmetics, February-2009, page 18-19) uses Lumorol K 1000 (MIPA laureth sulphate with Laureth-4 and CDEA, from Zschimmer and Schwarz) along with olive oil. For bath oil formulation, Zschimmer and Schwarz also offer TIPA laureth sulphate under the trade name of Zetesol TP 300.

Formula I

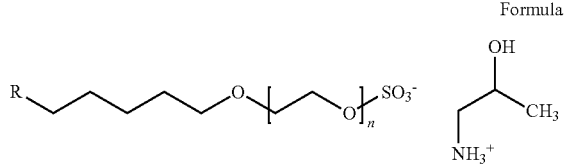

It is interesting to note that No 7 Luxurious Foaming oil uses MIPA laureth sulphate as anionic surfactant whereas Eucerin Calming Foaming Shower Oil has MIPA laureth sulphate along with CDEA. L'Occitane's Almond Supple Shower Oil has TIPA laureth sulphate with cocomonoethanol amide (CMEA).

In summary, both triglyceride oil based formulations for hair cleansing and for skin cleansing, employ oil-soluble or oil-suitable surfactants that are mainly based on aliphatic amine neutralized acyl sarcosines or aliphatic amine neutralized fatty alcohol/alcohol ether sulphate (U.S. Pat. No. 4,371,548). Amongst several amines mentioned above, the most widely used seem to be isopropanol amines, MIPA and TIPA (U.S. Pat. No. 6,132,738). Also, as mentioned above, these amine neutralized anionic surfactants are offered along with alkanol amides, CMEA and CDEA (U.S. Pat. No. 5,653,988). These amides are known for the possibility of generation of cancerous nitrosamine (N-nitrosodiisopropanol amine). If ethanol amines (mono, di, and tri ethanol amines) are prone to nitrosamine generation then by the same logic isopropanol amines are also prone to nitrosamine generation. (M. L. Douglass, The chemistry of nitrosamine formation, inhibition and destruction, *J. Soc. Cosmet. Chem.*, 29, 581-606, (1978)).

Ethanol amine based products like Cocodiethanol amide are banned (http://oehha.ca.gov/prop65/prop65_list/Newlist.html) due to possibility of carcinogenic nitrosoamines. Analogously, same possibility exists for Isopropanol amines as well. Just like diethanol amine, diisopropanol amine is also a carcinogen as reported by the German scientists and again recently confirmed by the Japanese scientists (W. Kriuger, *Naturwissenschaften*, 61 (1974), pp: 328), Toshifumi Tsujiuchi, *Experimental and Toxicologic Pathology*, 66 (2014), pp: 81-88).

It is also pertinent to mention here about the study of marketed shower oils reported by Marie Loden et al. (British Journal of Dermatology, 1142-1147, 150, (2004)). It has been reported that the shower oils with MIPA (Monoisopropanol amine) laureth sulphate irritates skin in patch test and such formulation may induce subclinical injuries and pose a serious risk for patients with eczema.

The shower oils are reported to leave a thin layer of occlusive oil and that raises the concern for not just irritation potential but also for the possible danger of aliphatic amines permeating through skin. In view of these serious concerns arising out of use of surfactants based on aliphatic amines, there is a definite need to develop oil based compositions for both skin and hair cleansing, without aliphatic amine neutralized anionic surfactants.

In summary, skin cleansing compositions containing high oil and that are substantially anhydrous (U.S. Pat. Nos. 5,653,988, 6,132,738, 6,620,773, EP1955690, U.S. Pat. No. 8,383,090, US20140256608) use anionic (fatty alcohol ether sulphates) and/or non ionic (alkanolamides) surfactants based on small chain amines or hydroxyl amines (mono ethanol amine, diethanol amine, diethyl amine, monoisopropanol amine, diisopropanol amine, triisopropanol amine, amino methyl propanol or amino propane diols). These aliphatic small chain amines based surfactants are required for oil solubility as well as for foaming. Even others are not so substantially anhydrous, oil based cleansers do deploy amine based surfactants (U.S. Pat. Nos. 4,371,548 A, 7,357, 922 B1). There is one recent relevant art that discloses oil based compositions without using aliphatic amine-based anionic surfactant (EP2839827). This European patent application deploys alkali salt of alkyl ether carboxylates. However, it should be noted that Alkyl ether carboxylates are not easily available compared to alkyl ether sulphates. These are significantly more costly compared to alkyl ether sulphates and hence very rarely used in personal care products. Though both anionic surfactants are made from fatty alcohols, alcohol ether sulphates are manufactured by continuous process with quantitative conversions and yields.

Hair Care Products The protective effect of coconut oil on hair against the damage that happens during grooming processes is well established. Coconut oil is used as a pre-wash conditioner and is reported to be significantly superior to mineral oils and other vegetable oils (A. Rele, Effect of coconut oil on prevention of hair damage. Part I, *J. Cosmet. Sci.*, 50, 327-339 (1999). It not only has a protective effect on undamaged hair but also on damaged hair due to either chemical treatment or solar UV radiation or even by hot water. The ability of coconut oil to penetrate into hair cuticle and cortex seems to be responsible for this effect. Penetration of coconut oil into cuticles and cortex seems to prevent or reduce the amount of water penetrating into cortex and thereby reducing the swelling of hair. This in turn reduces the lifting of the surface cuticle due to hydration and prevents it from being chipped away during wet combing. (S. B. Ruetsch, Y. K. Kamath, A. S. Rele and R. B. Mohile, Secondary ion mass spectrometric investigation of penetration of coconut and mineral oils in human hair fibers: Relevance to hair damage, *J. Cosmet. Sci.*, 52, 169-184 (2001) and A. S. Rele and R. B. Mohile, Effect of mineral oil, sunflower oil, and coconut oil on prevention of hair damage, *J. Cosmet. Sci.* 54, 175-192 (2003).

This is the reason why coconut oil is by far the most common oil used in Asia and Middle East and Africa for hair care. Prolonged use of coconut oil is known to lead to healthy looking long hair, suggesting that it may prevent damage to cuticle in grooming procedures involving abrasion (K. Keis, D. Persaud, Y. K. Kamath and A S Rele, Investigation of penetration abilities of various oils into human hair fibers, *J. Cosmet. Sci.*, 56, 283-295 (2005). It has been recently shown by Kamath et al. that coconut oil is best suited to penetrate the cuticle of hair fibers and leave a very thin layer of oil on the surface. This results in reduced moisture gain during washing with water and thereby reducing the swelling of cuticles and subsequent damage during wet combing. (K. Keis, C. L. Huemmer, and Y. K. Kamath, *J. Comset. Sci.*, 58, 135-145 (2007)). Thus, the science behind the use of coconut oil as pre-wash conditioner has been established during the period from year 1999 to 2007. However, the fact is that this habit of oiling the hair is quite ancient and is widely practiced by around 800 million people across central Asia and Middle East region. Patent Application US2008/0311062 by Kelvin Brian Dickinson et al. reports water-in-oil type of emulsions (cream like) for hair treatment. The compositions reported in this patent application are regular opaque macro-emulsions. The compositions of Dickinson's patent application neither have the transparency nor the look or feel of a typical 'hair oil' composition. Moreover, these water-in-oil types of emulsion compositions are for post-wash oiling of hair and are not meant for cleansing the hair. A recent patent application by Bailey et al. (WO2013/037752) teaches cleansing coconut oil composition that performs both the steps of 1) pre-wash conditioning and 2) subsequent cleansing of hair with water. The compositions of this patent application are reported to be good conditioners without any greasy feel. The oil-soluble compositions are said to be clear and look and feel like typical 'hair oil' compositions available in market. The foaming oil compositions of WO2013/037752 comprise of 50 to 90% of oil component and 10 to 50% of surfactant. The oil component is made up of triglyceride oil and other fatty ester oils. The surfactant component is made up of non-ionic surfactants and anionic surfactants. These compositions are completely oil-based and involve solubilizing the constituent members in the oil to get the clear solution. Since these are solutions in oil and without any water or with very negligible water content, the preferred water content in these compositions is less than 1.0% w/w. The surfactant, either alone or in combination with adjuvants, is required to be oil-soluble. The anionic surfactant that is needed for subsequent cleansing after pre-wash conditioning of hair must be amenable to dissolution in triglyceride oil. Hence, the selection of anionic surfactants is narrowed down and restricted to a few anhydrous surfactants that are amenable to dissolution in triglyceride oils. For example, anionic alkyl ether sulphates that can be used in the triglyceride oil composition are restricted to mono isopropanol amine lauryl ether sulphate (MIPA laureth sulphate, CAS No. 83016-76-6) or triisopropanol amine lauryl ether sulphate (TIPA laureth sulphate, CAS No. 107600-36-2). The amines are the cations of the anionic surfactants, the fatty alcohol ether sulphates as shown in Formula I.

Mono-, di- and tri-isopropanol amines laureth sulphates have been solubilized in coconut oil that is applied on hair as pre-wash conditioner (WO 2013/037752). Often times after applying coconut oil to hair, consumers do not wash hair immediately. In fact some consumers, particularly Asian women with long hair apply hair-oil at night before they go to bed and wash their hair in the morning. Thus, hair oil application is not a classical rinse-off procedure. Consumers massage their hair with coconut oil thoroughly and allow time for oil to be absorbed by scales of cuticles and then hair is washed with anionic surfactant. What it means is that if one is going to use coconut oil containing organic amines such as MIPA or TIPA (WO 2013/037752) then the later would remain on the scalp for a significant length of time, varying from a few minutes to a few hours depending upon the consumer practice. Also massaging action as well as coconut oil's well-known penetration ability can make MIPA like organic amines to diffuse through skin of scalp. Since the foaming oil compositions described in WO2013/037752 are supposed to be 'leave-on' for some time and then after a while these are rinsed off. Hence, use of organic amines with toxic properties (MSDS available from manufacturers like BASF/Dow Chemicals) on scalp can be very hazardous.

The prior art in its entirety having the cascading disadvantages as below:

The oil-based compositions are in vogue because they do the adequate cleansing without damaging the skin or hair.

Such oil based compositions are prepared using surfactants that have to be necessarily oil-soluble.

To make anionic surfactant amenable to all-oil based compositions, one is forced to use aliphatic amines like mono isopropanol amine (MIPA) or triisopropanol amine (TIPA). However, these surfactants are needed to avoid as these are potential source of carcinogenic nitrosamines and hence the possibility of toxicity arising out of percutaneous absorption is inevitable and hence necessitating for safer alternatives.

Further these oil based compositions provides high amount of lather, which results in heavy consumption of water while washing.

Also preparation of oil based formulations incurs expending of high energy so as to make them soluble in the anionic surfactants.

Thus, it is important that for hair conditioning-cum-cleansing coconut oil composition, which is both leave-on and rinse-off type of application, should have ingredients that are safe with regard to percutaneous absorption through scalp. Hence there is a need for oil compatible anionic surfactants that would be absolutely safe with respect to the possibility of diffusion through the skin of scalp. This need is addressed by water-in-oil microemulsions of the present patent application since the water-in-oil microemulsion form of oil compositions allows use of safer, well established anionic surfactants without diminishing the desired performance of coconut oil on hair.

OBJECT OF INVENTION

It is an objective of the present invention to create oil based cleansers for personal care without using oil-soluble anionic surface active agents that are salts of aliphatic amines. The goal is to avoid all sorts of amines, aliphatic or aromatic, that have potential to be source for generation of carcinogenic nitrosamines in addition to being toxic by themselves.

Another objective of the present invention is to replace aliphatic amine based anionic surfactants by safer equivalent surfactants that would be suitable for oil-based cleansers.

It is also an objective of this patent application to employ the anionic surfactants that have several decades-long safety track record while creating triglyceride-oil based hair and skin cleansing compositions.

It is a further objective of the present invention to create transparent, stable triglyceride oil based microemulsions for personal care products.

In yet another object, the invention provides the microemulsions that can be used even in pharmaceutical industry for drug delivery due to its absolute safety aspects.

SUMMARY OF INVENTION

In accordance with the above objectives, the present invention provides transparent water-in-oil microemulsion composition for personal cleansing comprising of:
a) 5 to 15% by weight of water;
b) 10 to 25% by weight of an anionic surfactant wherein the counter cation is selected from inorganic alkali and basic amino acids;
c) 15 to 30% by weight of triglyceride oil;
d) 40 to 65% by weight of non-ionic surfactants of Formula II, wherein RCO is the acyl group derived from fatty acids of vegetable oils and x+y+z can be any number between 2 to 6.

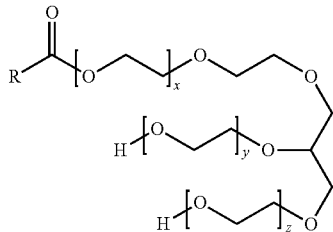

Formula II

The triglyceride oil in accordance with the invention is selected from coconut oil, soya oil, sunflower oil, palm kernel oil, olive oil, fish oil and mixtures thereof. In an aspect, the triglyceride oil is blended with a non-triglyceride oil.

According to the invention, the non-ionic surfactant of Formula II is preferably polyethylene glycol-7-glyceryl cocoate, RCO is the acyl radical of coco fatty acid, sunflower fatty acid or soya bean fatty acids and x+y+z=2 to 6.

According to the invention, the anionic surfactant is selected from the group consisting of sodium lauryl ether sulphate, L-Argininium lauryl ether sulphate or L-Argininium N-acyl amino acid.

The basic amino acid as used according to the invention is selected from Lysine, Histidine or Arginine.

In another aspect, the invention provides transparent compositions for use in skin cleansing formulation, hair cleansing formulation and hair care formulations.

In yet another aspect, the invention provides hair care formulations prepared using the transparent microemulsion composition of the invention, wherein vegetable oil is preferably coconut oil and non-ionic surfactant of Formula II is preferably PEG-7-glyceryl cocoate.

The transparent compositions of the present patent application find application in foaming shower oils for gentle skin cleansing. The compositions described in this patent application are used in 'two-in-one' hair oil preparation for pre-wash conditioning and then cleansing with water.

The above described features and advantages of the present disclosures will be appreciated and understood by those skilled in the art from the detailed description and the claims.

DESCRIPTION OF DRAWINGS

FIG. 1 depicts reduction in combing force measured during wet combing using DiaStron tensile tester for the composition of example 1 as it is for the application of coconut oil and subsequent cleansing with a shampoo (SLES—Cocamidopropyl betaine).

DETAILED DESCRIPTION OF INVENTION

The present invention provides transparent, water-in-oil microemulsion composition for personal cleansing comprising of
a) 5 to 15% by weight of water;
b) 10 to 25% by weight of an anionic surfactant wherein the counter cation is selected from inorganic alkali and basic amino acids;
c) 15 to 30% by weight of triglyceride oil;
d) 40 to 65% by weight of non-ionic surfactants of Formula II, wherein RCO is the acyl group derived from fatty acids of vegetable oils and x+y+z=2 to 6

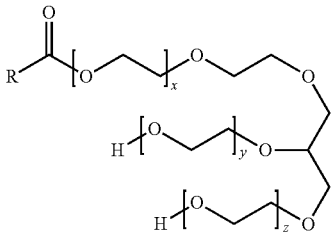

Formula II

The typical composition of the present patent application comprises of water, an anionic surfactant, a non-ionic surfactant and triglyceride oil. The water-in-oil compositions described in this patent application have 5 to 15% of water by weight, microemulsified in 15 to 30% by weight of vegetable (triglyceride) oils with the help of anionic surfactant ranging from 10 to 25% by weight along with a non-ionic surfactant ranging from 40 to 65% by weight of composition (Table 1). All the 16 microemulsions of Table 1 are transparent, as indicated by the Nephelometric Turbidity Units (NTU) value of less than 10.

The general procedure for making microemulsions is given in the Experimental section and it involves simple mixing of all ingredients at room temperature for a few minutes to achieve the homogeneity. The ease of formation of microemulsion is indicative of formation of a thermodynamically stable system.

eride oil at time, it is possible to use mixture of vegetable oils. Triglyceride type vegetable oils can be partly replaced by mineral oils like paraffin (Examples 14 & 16, Table 1) that is majorly hydrocarbon in the microemulsions of the present application. Example 14 shows 25% coconut oil has been replaced by liquid paraffin when compared with Example 1. Coconut oil is sometimes mixed with small portion of liquid paraffin to reduce its tackiness on hair in commercially available hair oil compositions (example, Parachute Jasmine Perfumed Non-sticky Coconut Hair Oil by Marico). The ratio of coconut oil to light paraffin oil is reversed in Example 16 wherein significantly higher amount of hydrocarbon is mixed with smaller quantity of coconut oil (4:1 by weight).

TABLE 1

| Ingredients | 1 | 2 | 3 | 4 | 5 | 6 | 7 | 8 | 9 | 10 | 11 | 12 | 13 | 14 | 15 | 16 |
|---|---|---|---|---|---|---|---|---|---|---|---|---|---|---|---|---|
| SLES (1EO) | 15 | 20 | 15 | 15 | 15 | 15 | 15 | 15 | 15 | | | | 15 | 15 | 15 | 15 |
| SLES (2EO) | | | | | | | | | | | | 12 | | | | |
| Argininum Laureth sulphate (1EO) | | | | | | | | | | 10.5 | | | | | | |
| PEG-7-gly-cocoate | 52.4 | 47.6 | 48.6 | | | | | | | 54 | 56.6 | 52.4 | | 52.4 | 52.4 | 52.4 |
| PEG-7-gly-soyate | | | | 52.4 | 52.4 | 52.4 | | | | | | | | | | |
| PEG-7-gly-sunflowerate | | | | | | | 52.4 | 52.4 | 52.4 | | | | 52.4 | | | |
| Coconut oil | 26.2 | 23.8 | 30 | | 26.2 | | | 26.2 | | 27 | 26.2 | | | 19.65 | | 5.2 |
| Soya oil | | | | 26.2 | | | 26.2 | | | | | | | | | |
| Sunflower oil | | | | | | 26.2 | | | 26.2 | | | | | | | |
| Palm Kernel oil | | | | | | | | | | | | 26.2 | | | | |
| Olive oil | | | | | | | | | | | | | 26.2 | | | |
| Light liquid paraffin | | | | | | | | | | | | | | 6.55 | | 21 |
| Sardine Fish Oil | | | | | | | | | | | | | | | 26.2 | |
| Water | 6.4 | 8.6 | 6.4 | 6.4 | 6.4 | 6.4 | 6.4 | 6.4 | 6.4 | 8.5 | 5.2 | 6.4 | 6.4 | 6.4 | 6.4 | 6.4 |

<10, Transparent

The W/O type of microemulsions of the present invention are absolutely transparent (NTU<10) at room temperature (25° C.). The viscosity of the most microemulsions is between 250 to 2000 cps at room temperature, depending upon the constitution. Also, depending upon the triglyceride oil and its fatty acid composition (chain length and unsaturation), the freezing point and cloud point can vary. For example, microemulsion of coconut oil typically freezes at temperatures below 20° C. (Example 1 of Table 1). However when coconut oil is mixed with paraffin then the freezing point or the solidification point is significantly lowered (Example 16 of Table 1) to about 0° C. Also, a microemulsion made with triglycerides having unsaturated fatty acids and the non-ionic PEGylated esters having unsaturated fatty acids can have low freezing points. This is illustrated by the microemulsion of Example 7 with soya oil and PEG-7-Glyceryl sunflowerate that has solidification point well below 0° C. Similarly, a perfect microemulsion is obtained with sunflower oil and PEG-7-Glyceryl sunflowerate with solidification very close to 0° C. The particle size analysis done by light scattering technique using Malvern Zetasizer was found to be in the range of 250 to 300 nm.

Triglyceride Oils that can be Used the Present Microemulsions

The vegetable oils that are used in making the compositions of the present invention can be selected from one or more of triglyceride oils like coconut, corn, cottonseed, canola, almond, sesame, peanut, soya, apple seed, pumpkin seed, castor, argan, macadamia, cotton seed, morango, palm kernel, sunflower, safflower seed, meadowfoam seed, and Tung oils. Table 1 shows examples of water-in-oil microemulsions with coconut oil, soya bean oil, sunflower oil, palm kernel oil and olive oil (Table 1, Examples 1, 4, 6, 12, and 13). Though the fourteen examples of Table 1 (Examples 1-13 & 15) show incorporation of only one triglyc- Triglyceride oils of any type are suitable for the microemulsions of this patent application. Triglyceride oils from other natural sources, like fish oils are also suitable. Example No. 15 shows microemulsion with Sardine oil (ZD 3020 TG, from Arjuna Natural Extracts Ltd, India, http://www.arjunanatural.com) that contains triglyceride of poly unsaturated fatty acids, Omega-3 acids—EPA (Eicosapentaenoic acid), and DHA (Decosahexaenoic acid).

Anionic Surfactants that can be Used the Present Microemulsions:

Anionic surfactant like sodium laureth sulphate is the most widely used cleansing agent in shampoos and body washes world over. However, it is impossible to solubilize ionic surfactant like sodium laureth sulphate (SLES) in triglyceride oils to make oil based skin cleansing or hair cleansing compositions. The W/O microemulsion compositions of the present patent application allow dissolution of the anionic surfactants like SLES in triglyceride type vegetable oils.

The anionic surfactants include the most commonly used cleansers for hair, sodium laureth sulphate. In this class the variants are available commercially with different degree of ethoxylation ranging from 1 EO to 4 EO. Table 1 shows Examples 1 to 9 using sodium laureth sulphate with 1 EO and Example 11 using sodium laureth sulphate with 2 EO.

These are conventional anionic surfactants that are widely used and are easily available all over the world from several manufacturers. These fatty alcohol ether sulphate salts are difficult to solubilize in triglyceride oil compared to the amine neutralized laureth sulphate such as MIPA laureth sulphate and TIPA laureth sulphate that are more amenable to solubilization in triglyceride oils.

However, the inventors of the present application have surprisingly discovered that surfactants like sodium lauryl ether sulphate (SLES), that are otherwise insoluble in triglyceride oil, can be solubilized in vegetable oils in the form of W/O microemulsion. W/O microemulsions of the present patent application allows use of anionic surfactants with sodium as cation and yields transparent formulation with oil as continuous phase. It is possible to create shower oil formulations as well as hair oil formulations using SLES. Most of the commercial and commonly used anionic surfactants are available as sodium salts, however, surfactant with potassium as counter cation can be used with equal ease while creating W/O microemulsions.

Since the compositions of this patent application based on coconut oil are targeted for hair care where, after oiling of hair with massaging action, the hair oil is rinsed off. In such cases of short term leave-on' step, use of the aliphatic amine neutralized ether sulphates or sarcosinates is not a good idea for the reasons cited above. Hence sodium salt of laureth sulphate or L-Argininium salt of laureth sulphate can be used (Formula III). Example 10 in Table 1 shows microemulsified water in coconut oil using Arginine neutralized laureth sulphate. L-Arginine is the one of the non-essential amino acids and very abundantly found in hair protein. It is used as dietary supplement and widely used in hair care products. Hence Arginine, the natural amino acid is expected to be significantly safer than other organic amines (MIPA, TIPA, AMP etc) that are used in making of anionic surfactants with respect to the possible adverse effects that might arise due to percutaneous absorption. Similarly, other basic amino acids like L-lysine or L-histidine can be used to neutralize alkyl sulphonic acids, sulphates or carboxylic acids.

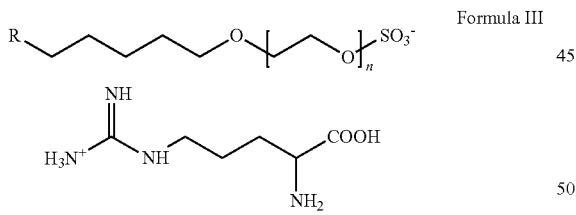

Formula III

Argininium laureth sulphate (Formula III) (R=C$_7$) was prepared by adding laureth (1 EO) sulphate (one equivalence) (prepared by reacting lauryl alcohol ethoxylate and sulphur trioxide) to a stirred aqueous solution of L-Arginine (one equivalence) at room temperature to get solution with active content of 30-35%. Table 1 shows examples of W/O type of microemulsions using fatty alcohol ether sulphate as anionic surfactants. Table 2 shows examples of W/O emulsions (Example 17, 18, 19 and 20) employing anionic surfactants other than fatty alcohol ether sulphates, for example, sodium N-oleoyl sarcosinate or L-Argininium N-cocoyl glycinate. Argininium amino acid surfactants are synthesized by neutralizing N-amino acids like N-cocoyl glycine or N-lauroyl sarcosine with basic amino acid, L-Arginine (Formula IV and Formula V).

Formula IV

RCO = Cocoyl

Formula V

RCO = Lauroyl

The Argininium amino acid surfactants have been used to create W/O microemulsion with soya oil that is quite popularly used in liquid skin cleansers (Example no. 19, Table 2).

TABLE 2

| Example No. | 17 | 18 | 19 | 20 |
|---|---|---|---|---|
| Ingredients | | | | |
| L-Argininium N-Cocoyl Glycinate | | 14.4 | 15 | |
| Sodium N-oleoyl Sarcosinate | 10 | | | 15 |
| PEG-3 Glyceryl Cocoate | 49.5 | 57.8 | 52.4 | 52.4 |
| Coconut Oil | 25.5 | 19.3 | 26.2 | |
| Soya bean Oil | | | | 26.4 |
| Water | 15 | 8.5 | 6.5 | 6.2 |
| | | NTU < 10 | | |

Examples 1 to 9 and examples 11 to 16 teach the use of anionic surfactants that are sodium salts. In industrial surfactant manufacturing, use of sodium hydroxide is very common. Analogously, potassium salts of anionic surfactants can be used in creating microemulsion of the present invention, instead of sodium salts. Similarly, ammonium salts of anionic surfactants are also quite prevalent in personal care applications. Examples (No. 21-25) listed in Table 3 show the compositions of isotropic stable microemulsions using ammonium salts of anionic surfactants, namely, ammonium laureth sulphate and ammonium lauroyl sarcosinate.

TABLE 3

| Example No | 21 | 22 | 23 | 24 | 25 |
|---|---|---|---|---|---|
| Ingredients | | | | | |
| Ammonium Laureth Sulfate (1EO) | 15 | 15 | | | |
| Ammonium Lauroyl Sarcosinate | | | 15 | 15 | 15 |

TABLE 3-continued

| Example No | 21 | 22 | 23 | 24 | 25 |
|---|---|---|---|---|---|
| PEG-3-Caprylic/Capryl monoglyceride | 26.2 | 13.1 | 52.4 | 52.4 | 26.2 |
| PEG-3-gly-soyate | 26.2 | 13.1 | | | |
| Caprylic Capric Triglycerides | 13.1 | 13.1 | 26.2 | | 26.2 |
| Soybean Oil | 13.1 | 13.1 | | 26.2 | |
| Laureth-3 | | 26.2 | | | 26.2 |
| Water | 6.4 | 6.4 | 6.4 | 6.4 | 6.4 |

Non-Ionic Surfactants Used in the Present Microemulsions:

The non-ionic surfactants used in the composition of the present patent application is selected from fatty acid esters of glyceryl ethoxylates (3 to 7 EO), Formula II, wherein RCO is the acyl group derived from fatty acids of vegetable oils and x+y+z=2 to 6.

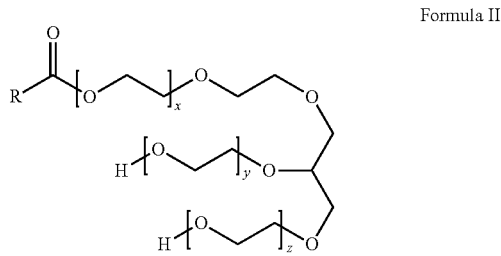

Formula II

The most common member of this group is Polyethylene glycol (PEG)-7-glyceryl cocoate (CAS No. 68201-46-7). Table 1 shows the examples of water-in-oil microemulsions with three non-ionic surfactant of Formula II. These have been synthesized by esterifying glycerin ethoxylate (3 to 7 moles of Ethylene Oxide) with fatty acids derived from vegetable oils. According to illustrative examples of Table 1 and 2, coco fatty acid, sunflower fatty acid and soya fatty acid have been used to create non-ionic surfactants of Formula II. Experimental section describes the general method of synthesis of compounds of Formula II and the analytical parameters (Table 6).

Lower degree of ethoxylation in case of compounds of Formula II, resulted in stable transparent microemulsions as exemplified by Table 3 with PEG-3-Caprylic/Capryl monoglyceride (CAS no. 1859954-64-5) and PEG-3-glyceryl soyate (CAS no. 1859954-61-2) as well as in Table 4 with PEG-3 glyceryl cocoate (CAS no. 1859954-15-6) and PEG-5 glyceryl cocoate. Other non-ionic surfactants like Laureth-3 (lauryl alcohol 3 mole ethoxylate, CAS No. 3055-94-5), Laureth-7 (lauryl alcohol 7 mole ethoxylate, CAS No. 3055-97-8) and dilaureth-7 citrate (CAS no. 141250-39-7) yielded very stable and transparent W/O microemulsion as shown in Examples 28 to 30 (Table 4).

TABLE 4

| Ingredients | 1 | 26 | 27 | 28 | 29 | 30 |
|---|---|---|---|---|---|---|
| Sodium Laureth Sulfate (1EO) | 15 | 15 | 15 | 15 | 15 | 15 |
| PEG-3-glyceryl Cocoate | | 52.4 | | | | |
| PEG-5-glyceryl Cocoate | | | 52.4 | | | |
| PEG-7-glyceryl Cocoate | 52.4 | | | | | |
| Dilaureth-7 citrate | | | | 52.4 | | |

TABLE 4-continued

| Ingredients | 1 | 26 | 27 | 28 | 29 | 30 |
|---|---|---|---|---|---|---|
| Laureth-3 | | | | | 52.4 | |
| Laureth-7 | | | | | | 52.4 |
| Coconut Oil | 26.2 | 26.2 | 26.2 | 26.2 | 26.2 | 26.2 |
| Water | 6.4 | 6.4 | 6.4 | 6.4 | 6.4 | 6.4 |
| NTU < 10, Transparent | | | | | | |

Table 5 shows attempted microemulsions with compounds of Formula II wherein R is cocofatty acid and x+y+z is equal to 10 and 14. In most cases the compositions were translucent and not transparent. The higher degree of ethoxylation in compounds of Formula II does not seem to favor the clean, thermodynamically favorable W/O microemulsion formation. The most preferred non-ionic surfactants of the W/O microemulsions of these patent application are compounds of Formula II with x+y+z=6. PEG-7 glyceryl cocoate is well-, known emollient and skin conditioning agent for personal care applications. It is reported to replenish the lost lipids of stratum corneum during the cleansing process. Sunflower oil and soya oil are very widely used as skin benefit agents in leave-on and rinse-off formulations. The compounds of Formula II derived from sunflower fatty acid or soya fatty acid or oleic acid are good emollients and are currently used by personal care industry. The safety report by Cosmetic Ingredient Review (CIR) committee (http://www.cirsafety.org/ingredients) discusses the entire family of PEGylated alkyl glycerides. This review report mentions that PEG-7 glyceryl cocoate to be the most widely used and discusses the safety evaluation data in detail. The latest report from CIR mentions about 60 PEGylated alkyl glycerides derived from variety of triglycerides like almond, olive, sunflower, soya, shea butter, avocado, corn, babassu, palm, primrose, macadamia, mango, moringa, mushroom, passion flower, safflower, mink and fish and with PEG numbers ranging from to 2 to 60. Generally PEGylated alkyl glycerides have been reported to be safe and nothing untoward seems to be reported in literature about this class of emollients. In HETCAM (Hen's egg test using chorioallantoic membrane) a formulation containing 11% of PEG-7 glyceryl cocoate was non-irritant. 100% PEG-7 glyceryl cocoate is reported as slightly irritating by HETCAM. Similarly, PEG-10 sunflower glyceride is reported to be a non-irritant in a chorioallantoic membrane vascular assay.

TABLE 5

| Ingredients | 31 | 32 | 33 | 34 | 35 | 36 |
|---|---|---|---|---|---|---|
| Sodium Laureth Sulfate (1EO) | 15 | 15 | 15 | 15 | 15 | 15 |
| PEG-10 Glyceryl Cocoate | 52.4 | | | | | |
| PEG-10 Glyceryl Soyate | | 52.4 | | | | |
| PEG-10 Glyceryl Sunflowerate | | | 52.4 | | | |
| PEG-14 Glyceryl Cocoate | | | | 52.4 | | |
| PEG-14 Glyceryl Soyate | | | | | 52.4 | |
| PEG-14 Glyceryl Sunflowerate | | | | | | 52.4 |
| Coconut Oil | 26.2 | 26.2 | 26.2 | 26.2 | 26.2 | 26.2 |
| Water | 6.4 | 6.4 | 6.4 | 6.4 | 6.4 | 6.4 |
| NTU > 10, Translucent | | | | | | |

As it is known that regular application of coconut oil as pre-wash conditioner promotes healthy hair. However, coconut oil applied to hair needs to be rinsed off by a cleansing formulation like a shampoo. Thus, shampooing is a separate operation that is followed after oiling of hair.

The W/O microemulsions of vegetable oils provided by the present invention are suitable for hair oil compositions. Moreover, the compositions of the present invention based on coconut oil (Table 1, Example no. 1) offers the convenience of both oiling of the hair and cleansing of the same. The prewash conditioning effect of composition of Example 1 on hair is as good as 100% coconut oil. This has been established by measuring the combing force reduction using DiaStron tensile tester (FIG. 1). The reduction in combing force measured while during wet combing is about the same for composition of Example 1 as it is for the application of coconut oil and subsequent cleansing with a shampoo (SLES—Cocamidopropyl betaine). FIG. 1 confirms that the composition of example 1 not only gives the convenience of 'two-in-one' operation (leave-on and rinse-off) but also the conditioning performance that is at par with coconut hair oil.

For this kind of 'two-in-one' formulation, cleansing agent must be formulated with coconut oil in such a way that the composition performs like typical hair oil, which is achieved with W/O type of microemulsion of Example 1 that is used in creating hair formulations (Example no. 38 and 39). W/O microemulsions based on Argininium laureth sulphate and coconut oil (Example no. 10) are used for preparing hair formulations (Example no. 40). These 'two-in-one' type 'conditioner cum cleanser' hair-oil formulations are prepared with adjuvants like vitamins, proteins hydrolyzates and amino acids. Examples of suitable amino acids that can be selected to create hair care formulations using compositions of the present invention are arginine, cysteine, glutamine, glutamic acid, isoleucine, leucine, methionine, serine, valine and/or their precursors and derivatives. Peptides can be di-, tri-, tetra- etc. or oligopeptides or they can be in the form of protein hydrolyzates. Examples of protein hydrolyzates are milk, silk, keratin and collagen (animal derived) or Quinoa, Baobab, Barley, Flax, Wheat, Rice etc. (vegetable derived) as listed in product brochure of Tri-K Industries (www.tri-k.com). The adjuvants can be natural hair root nutrients that include sugars, honey, and vegetable and herbal extracts, Bhringaraj oil or calendula oil that supports hair growth.

Other hair fiber benefit agents that can be included in hair care formulations using microemulsions of the present application are ceramides that are normally used for maintaining cuticle integrity. These ceramides are derived either from nature or they can be of synthetic origin. Synthetic humectants can be selected from sorbitol, glycerin, panthenol, dipropylene glycol, sodium PCA, hyaluronic acid or its sodium salt.

Water-soluble silicones for gloss and water-soluble quaternary ammonium conditioners such as Guar hydroxypropyl trimethyl ammonium chloride, Polyquaternium 10 or Polyquaternium 11 can be added to hair oil formulation using the W/O microemulsions.

Water-soluble UV absorbers can be selected from UV-B as well as UV-A range. Examples are benzophenone-4,3-(N-p-methoxy cinnamidopropyl-N,N-dimethyl (CAS No. 500731-87-3) (Galaxy SunBeat) and Disodium phenyl dibenzimidazoletetrasulfonate. It is interesting to note that oil-soluble sunscreens like octyl methoxy cinnamate (OMC) and octocrylene can also be added. Microemsulsions of the present invention are able to incorporate both oil-soluble as well as water-soluble ingredients.

Skin cleansing oils (Examples 41, 42 and 43) have been prepared with W/O microemulsions of Example 4, 6 and 18. Microemulsions made with soya, sunflower oil are suitable for skin cleansing. Other useful triglyceride oils are primrose oil, avocado oil and almond oil for skin care. In skin cleansers oils (shower oils) part of vegetable oil can be replaced by petrolatum or vegetable butter like Shea. Other nutrients that can be used for strengthening as well as moisturizing the skin are vitamins A, E and alkyl ester of vitamin C. The other useful lipids are cholesterol, cholesterol ester, ceramides, pseudo-ceramides and phospholipids like lecithin. Antimicrobial oils like Tea tree oil and anti-acne molecules like salicylic acid and derma purifier like capryloyl glycine can be used in shower oil skin cleansers. Skin lightening and sunscreens, either oil-soluble or water-soluble can be added. Skin calming agent like Aloe vera and other herbal extracts and fruit juices can be incorporated in skin cleanser oils formulations that are made from W/O microemulsions of present patent application.

Essential oils for the shower oil formulations can be selected from jasmine, camphor, white cedar, orange peel, cinnamon, bergamot, calamus, pine, lavender, bay, clove, eucalyptus, lemon, thyme, peppermint, rose, sage, citral and citronella, borneol, thymol etc. The W/O type of microemulsions of the present invention are useful for preparing shower oils for babies. Currently some marketed products (Nivea baby pure and natural bath oil) use Monoisopropanol amine (MIPA) laureth sulphate as the anionic surfactant along with soya bean oil, castor oil liquid paraffin, cocodiethanol amide and Shea butter. This aliphatic amine is always a concern for the generation of carcinogenic corresponding N-nitrosodiisopropanolamine. Moreover, baby product can avoid fatty alcohol ether sulphate type products that generally have carcinogenic 1,4-dioxane (that gets generated during sulphation of ethoxylated fatty alcohol using sulphur trioxide). The W/O microemulsions of the present invention allows use of very safe anionic surfactants like Argininium cocoyl glycinate for cleansing of baby's sensitive skin (Example 43).

In the preparation of the skin and hair cleansing and hair care formulations, the W/O microemulsions of the present invention may be used in an amount of 85 to 99% w/w of the formulation.

Advantages

1) W/O microemulsions of the present invention allow the formulator to use simple, time-tested anionic surfactants like sodium lauryl ether sulphate (SLES), which the personal care industry has been using for skin cleansing formulation for over half century, thereby avoiding aliphatic amine based surfactants (and the alkanolamides that often times go with them).
2) The microemulsions of this patent application allow use of anionic surfactants like sulphates and carboxylates with the counter cations that are basic, naturally occurring amino acids such as L-Arginine.
3) W/O microemulsions of the present patent application allow the use of mild surfactants such as natural amino acid based Argininium cocoyl glycinate (avoiding harsh surfactants like ether sulphates or aliphatic amine salts) for shower oil formulations for the sensitive skin and for baby oils formulations.
4) W/O microemulsions of the present application are extremely facile to make (energy-efficient). It involves simple agitation at room temperature for very short time. Formation of microemulsion is a thermodynamically favorable process.
5) W/O microemulsions of the present application allow use of not only water-soluble surfactants but they also allow use of other water-soluble benefit agents (D/L-Panthenol, protein hydrolyzates, amino acids) that otherwise are difficult to formulate in all-triglyceride (oil-continuous) formulations.
6) W/O microemulsions of this patent application are amenable to both water-soluble and oil-soluble benefit agents for skin and hair.
7) W/O microemulsions of the present patent application allow low lather and gentle cleansing formulations. Low lather formulations consume less water while rinsing them off. Ease of rinsability and less water consumption are important aspects for overall sustainability.
8) W/O microemulsions of the present patent application allow 'two-in-one' hair conditioning cum cleansing hair oil formulations with coconut oil.
9) Coconut oil is rated as the best oil for hair care. 'Two-in-one' hair oil formulation based on microemulsion of the present application performs as good as separate oiling and shampooing procedure, when assessed by reduction in wet combing force.
10) In addition to the personal & home care sector, W/O microemulsions of the present invention also find application in pharmaceutical industry, as a medium for drug delivery.

EXAMPLES

The present invention is now described by way of working on non-limiting illustrative examples. The detail of the invention provided in the following examples is given by the way of illustration only and should not be construed to limit the scope of the present invention.

Examples 1 to 25 Disclosed in Tables 1 to 3: General Procedure for Preparation of Water-In-Oil Microemulsions of Vegetable Oils To a stirred mixture of water, anionic surfactant and non-ionic surfactant (Formula II) at room temperature, vegetable oil is added and stirring continued for 10 to 15 minutes till homogeneous transparent microemulsion is formed. Table 1 and 2 give 20 microemulsions using various triglyceride oils and using a variety of anionic surfactants. The non-ionic surfactants (Formula II) used in effecting microemulsions are made from coco fatty acid, soya fatty acid and sunflower fatty acid.

General Procedure for Synthesis of Non-Ionic Surfactants of Formula II

Synthesis of non-ionic surfactants (Formula II) is a two-step procedure:
a) Synthesis of glycerin ethoxylate (2 to 7 EO)
b) Reaction of glycerin ethoxylate with fatty acids derived from vegetable oils.

Step a) Synthesis of Glycerin Ethoxylate (2 to 7 EO)

Glycerin (1 mol) is reacted with ethylene oxide (2 to 7 mol) at 120° C. under base catalysis to obtain glycerin ethoxylate (2 to 7 EO) respectively.

Step b) Esterification of Vegetable Fatty Acid with Glycerin Ethoxylate:

A mixture of vegetable fatty acid (1 gmol), glycerin ethoxylate synthesized in step a) (1 gmol) and an acidic catalyst (0.2 mole %) is stirred at 130 to 140° C. for 4 to 5 h under slow purging of nitrogen. The water generated during the course of reaction is removed. Progress of the reaction is monitored by measuring the drop in the acid value of the reaction mixture.

TABLE 6

| | Appearance | Sap value | Acid value |
|---|---|---|---|
| PEG-7-gly-cocoate | Colorless liquid | 95.5 | 3.0 |
| PEG-7-gly-soyate | Pale yellow liquid | 88 | 8 |
| PEG-7-gly-sunflowerate | Pale yellow liquid | 83 | 8.0 |
| PEG-3-gly-cocoate | Colorless liquid | 148 | 4.9 |
| PEG-5-gly-cocoate | Colorless liquid | 124 | 5.5 |

Example 37: Comparative Measurement of Reduction in Combing Force Using Coconut Oil and Composition of Example 1

Pure Coconut Oil and composition of Example 1 (Table 1) is used for the study. Bleached Indian hair samples are used. 0.2 gm of Example 1 oil is placed on 2 gm hair swatches using syringe. The oil is massaged on the hair fibers with hand covered with gloves for 5 minutes. It is observed that negligible amount of oil is left over on the glove after application. The hair tresses are kept for 12 hours in a stability chamber maintaining a temperature of 25±0.5° C. and a relative humidity of 55±5. The hair samples treated with coconut oil are washed with shampoo (dilution to give 0.05% surfactant concentration, sodium lauryl ether sulphate and cocamide propyl betaine) and the hair that are treated with composition of Example 1 are washed with water for a minute. Combing force measurement is done on DiaStron MTT 175 apparatus. For wet combing, the reduction in combing force for hair strands treated with coconut oil and for hair strands treated with microemulsion of Example 1 is found to be comparable as shown in FIG. 1.

Example No. 38: Hair Oil Formulation with Water-In-Oil Microemulsion of Example No. 1

| Ingredients | % w/w |
|---|---|
| Microemulsion of Example 1(SLES, PEG-7-Gly cocoate, coconut oil and water) | 97.00 |
| DL-Panthenol | 1.0 |
| Vitamin E | 0.5 |
| Butylated hydroxyl toluene (BHT) | 0.1 |
| Phenoxy ethanol | 0.5 |
| Fragrance | 0.9 |

Example No. 39: Hair Oil Conditioning, Cleansing and UV Protection Formulation with Water-In-Oil Microemulsion of Example No. 1

| Ingredients | % w/w |
|---|---|
| Microemulsion of Example 1(SLES, PEG-7-Gly cocoate, coconut oil and water) | 96.5 |
| Galaxy SunBeat | 0.5 |
| DL-Panthenol | 1.0 |
| Vitamin E | 0.5 |
| BHT | 0.1 |
| Phenoxy ethanol | 0.5 |
| Fragrance | 0.9 |

Example No. 40: Hair Oil Conditioning and
Nourishing with Water-In-Oil Microemulsion of
Example No. 10

| Ingredients | % w/w |
|---|---|
| Microemulsion of Example 9 (Arginine Laureth ether sulphate, PEG-7-Gly cocoate, coconut oil and water) | 96.00 |
| DC 344 fluid (Cyclotetrasiloxane and cyclopentasiloxane) | 1.0 |
| DL-Panthenol | 0.5 |
| Vitamin E | 0.4 |
| BHT | 0.1 |
| Keratin protein hydrolyzate | 0.25 |
| Quinoa protein hydrolyzate | 0.25 |
| Phenoxy ethanol | 0.5 |
| Fragrance | 1.0 |

Example No. 41: Shower Oil with Water-In-Oil
Microemulsion of Example No. 4

| Ingredients | % w/w |
|---|---|
| Microemulsion of Example 4 (SLES, PEG-7-Gly Soyate, soya oil and water) | 96.00 |
| DL-Panthenol | 1.0 |
| Vitamin E | 0.5 |
| Cyclomethicone | 0.5 |
| Capryloyl glycine | 0.5 |
| BHT | 0.1 |
| Phenoxy ethanol | 0.5 |
| Fragrance | 0.9 |

Example No. 42: Preparation of Foaming Oil
Shower Bath with Water-In-Oil Microemulsion of
Example No. 6

| Ingredients | % w/w |
|---|---|
| Microemulsion of Example 6 (SLES, PEG-7-Gly Soyate, sunflower oil and water) | 97.4 |
| AEROSIL 200 | 0.5 |
| Essential oil blend (Artemisia, Citronella, Rosemary) | 1.0 |
| Vitamin E | 0.5 |
| BHT | 0.1 |
| Phenoxy ethanol | 0.5 |

Example No. 43: Preparation of Baby Shower Oil
with Water-In-Oil Microemulsion of Example No.
18

| Ingredients | % w/w |
|---|---|
| Microemulsion of Example 17 (Argininium cocoyl glycinate, PEG-7-Gly cocoate, coconut oil and water) | 97.4 |
| Ceramide-AP | 0.5 |
| Hydrolyzed Oat protein | 1.0 |
| Vitamin E | 0.5 |
| BHT | 0.1 |
| Phenoxy ethanol | 0.5 |

We claim:

1. A transparent water-in-oil microemulsion composition comprising
   a) 5 to 15% by weight of water, wherein the water is microemulsified;
   b) a triglyceride oil in an amount which is:
      greater than 15% by weight of the microemulsion composition; and
      up to and including 30% by weight of the microemulsion composition; and
   c) a mixture of surfactants, consisting of, based on the weight of the microemulsion composition:
      10 to 25% by weight of an anionic surfactant, wherein the counter cation is an inorganic alkali or a basic amino acid; and
      40 to 65% by weight of a non-ionic surfactant of Formula II, wherein RCO is the acyl group derived from fatty acids of vegetable oils and x+y+z=2 to 6

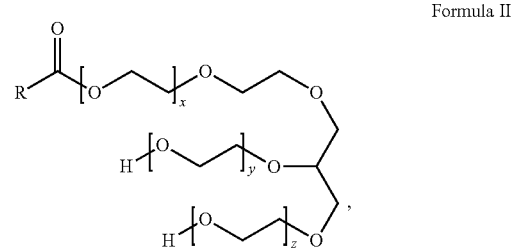

Formula II wherein the anionic surfactant and the non-ionic surfactant of Formula II are the only surfactants in the microemulsion formulation.

2. The transparent composition as claimed in claim 1, wherein the triglyceride oil is selected from the group consisting of coconut oil, soya oil, sunflower oil, palm kernel oil, olive oil, fish oil and mixtures thereof.

3. The transparent composition as claimed in claim 1, wherein the transparent composition further comprises a non-triglyceride oil.

4. The transparent composition as claimed in claim 1, wherein the non-ionic surfactant of Formula II is polyethylene glycol-7-glyceryl cocoate.

5. The transparent composition as claimed in claim 1, wherein the anionic surfactant is sodium lauryl ether sulphate.

6. The transparent composition as claimed in claim 1, wherein the anionic surfactant is L-Argininium lauryl ether sulphate.

7. The transparent composition as claimed in claim 1, wherein the anionic surfactant is L-Argininium N-acyl amino acid.

8. The transparent composition as claimed in claim 1, wherein the basic amino acid is Lysine, Histidine or Arginine.

9. A skin cleansing formulation comprising the transparent microemulsion composition of claim 1.

10. A hair cleansing formulation comprising the transparent microemulsion composition of claim 1.

11. A hair care formulation comprising the transparent microemulsion composition of claim 1, wherein the vegetable oil is coconut oil and the non-ionic surfactant of Formula II is PEG-7-glyceryl cocoate.

12. The transparent composition as claimed in claim 1, wherein, in the non-ionic surfactant of Formula II, RCO is an acyl radical derived from coco fatty acid, sunflower fatty acid, or a soya bean fatty acid.

13. A transparent water-in-oil microemulsion composition, comprising:
  a) 5 to 15% by weight of water, wherein the water is microemulsified;
  b) 15 to 30% by weight of triglyceride oil; and
  c) a mixture of surfactants, consisting of, based on the weight of the microemulsion composition:
    52.4% to 65% by weight of non-ionic surfactants of Formula II, wherein RCO is the acyl group derived from fatty acids of vegetable oils and $x+y+z=2$ to 6

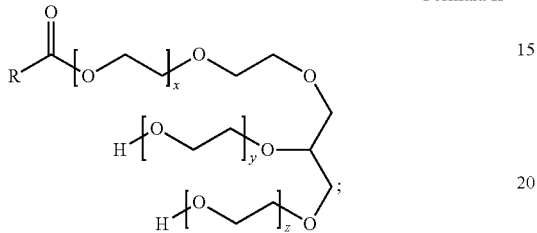

Formula II 10 to 25% by weight of an anionic surfactant wherein the counter cation is an inorganic alkali or a basic amino acid;
    wherein the anionic surfactant and the non-ionic surfactant of Formula II are the only surfactants in the microemulsion formulation.

* * * * *